United States Patent [19]

Goettsche et al.

[11] Patent Number: 4,871,473
[45] Date of Patent: Oct. 3, 1989

[54] WOOD PRESERVATIVE

[75] Inventors: Reimer Goettsche, Baden-Baden; Hans-Norbert Marx, Buehl-Vimbuch, both of Fed. Rep. of Germany

[73] Assignee: Dr. Wolman GmbH, Binzheim, Fed. Rep. of Germany

[21] Appl. No.: 285,614

[22] Filed: Dec. 16, 1988

[30] Foreign Application Priority Data

Dec. 17, 1987 [DE] Fed. Rep. of Germany ....... 3742834

[51] Int. Cl.$^4$ .................. C09K 15/16; C09K 15/22; C09D 5/18; A61K 33/30
[52] U.S. Cl. ........................... 252/400.52; 106/18.36; 252/401; 252/403; 252/405; 252/407; 252/602; 252/607; 424/DIG. 11; 424/640; 427/351; 427/397; 427/421; 427/440; 514/494
[58] Field of Search ................ 252/400.1, 400.52, 602, 252/607, 401, 407; 106/15.05, 18.36, 18.32; 427/439, 440, 351, 370, 305, 317; 424/133–134, 145, DIG. 10, DIG. 11

[56] References Cited

U.S. PATENT DOCUMENTS

| Re. 31,576 | 5/1984 | Hilditch | 424/145 |
|---|---|---|---|
| 3,454,514 | 7/1969 | Baum | 252/400.52 |
| 3,625,893 | 12/1971 | Brook et al. | 252/400.52 |
| 3,976,594 | 8/1976 | Dahlgren | 252/400.52 |
| 4,143,153 | 3/1979 | Pommer et al. | 424/289 |
| 4,193,993 | 3/1980 | Hilditch | 424/145 |
| 4,288,249 | 9/1981 | Amundsen et al. | 424/142 |
| 4,461,721 | 7/1984 | Goettsche et al. | 252/607 |
| 4,552,885 | 11/1985 | Gabriele et al. | 514/316 |
| 4,622,248 | 11/1986 | Leach et al. | 424/145 |
| 4,648,988 | 3/1987 | Van Dijck et al. | 252/602 |

FOREIGN PATENT DOCUMENTS

519146 10/1979 Australia .

*Primary Examiner*—Howard J. Locker
*Attorney, Agent, or Firm*—Oblon, Spivak, McClelland, Maier & Neustadt

[57] ABSTRACT

Wood preservatives which are based on a zinc compound and an aliphatic carboxylic acid and additionally contain a polyamine and processes for preserving wood with these preservatives.

16 Claims, No Drawings

WOOD PRESERVATIVE

The present invention relates to a wood preservative, for example in the form of an aqueous solution, which contains a zinc compound, an aliphatic carboxylic acid and a polyamine and may contain a complex-forming carboxylic acid.

Wood preservatives based on alkanolamine, copper compounds and aliphatic $C_6$–$C_{18}$-monocarboxylic acids are known (Australian Pat. No. 519,146). However, the copper-containing formulations produce a bluish green discoloration on the wood. Corresponding wood preservatives based on zinc compounds do not produce discoloration but are unstable in aqueous solutions and are precipitated.

We have found that the abovementioned disadvantages do not occur in wood preservatives based on zinc compounds, aliphatic carboxylic acids and polyamines, with or without a complex-forming carboxylic acid. Examples of particularly suitable polyamines in this case are aliphatic polyamines, alkylene polyamines of 3 to 9 carbon atoms and 2 to 4 nitrogen atoms, 1,3-diaminopropane, dipropylenetriamine (3,3'-diaminodipropylamine), ethylenediamine, diethylenetriamine (2,2'-diaminodiethylamine), and aminoethylethanolamine.

Examples of suitable aliphatic carboxylic acids are $C_5$–$C_{20}$-monocarboxylic acids, such as hexanoic acid, heptanoic acid, octanoic acid, nonanoic acid, decanoic acid, 2-ethylpentanoic acid, 2-ethylhexanoic acid, 2-ethylheptanoic acid, isooctanoic acid, isononanoic acid, isodecanoic acid or versatic acids (highly branched monocarboxylic acids), and $C_5$–$C_{20}$-dicarboxylic acids, eg. decanedicarboxylic acid. Polycarboxylic acids, such as polyacrylic acids, are also suitable.

These acids combine with zinc to form water-insoluble salts, which are dissolved in alkaline medium by the complex-forming action of the abovementioned amines. Complex formation can be improved by adding complex-forming carboxylic acids, eg. nitrilotriacetic acid or $C_3$–$C_6$-hydroxycarboxylic acids, lactic acid, tartaric acid or citric acid.

Suitable zinc compounds are water-soluble or insoluble compounds (eg. zinc metal, zinc sulfate, zinc hydroxide, zinc carbonate, zinc oxide, zinc acetate, zinc borate, zinc fluoride and zinc fluoroborate).

In concentrated form, the water-dilutable agents contain the zinc in an amount of 1 to 15% by weight, calculated as the element.

Anions capable of diffusion, eg. borates, fluorides or fluoroborates, may additionally be present, the said anions providing protection for regions not accessible to impregnation, such as the heartwood, as a result of their diffusion after impregnation of the wood.

The action of the wood preservative can be supported, for example, by salts of N-cyclohexyldioxydiazenium oxide, for example the zinc salt or the potassium salt. Combination with quaternary ammonium compounds is also suitable for this purpose.

A quaternary ammonium compound is, for example, a compound of the general formula $(R^1R^2R^3R^4N)^+Z^-$, where $R^1$ is alkyl of 8 to 20, in particular 12 to 20, carbon atoms or benzyl which is unsubstitued or substituted by $C_1$–$C_{20}$-alkyl or halogen, $R^2$ is $C_1$–$C_6$-alkyl or $C_3$–$C_9$-alkoxyalkyl, $R^3$ is $C_1$–$C_6$-alkyl or $C_1$–$C_{14}$-alkoxy and $R^4$ is $C_1$–$C_{20}$-alkyl, or two of the radicals $R^1$ to $R^4$ together with the nitrogen atom form a heterocyclic radical which contains 4 or 5 carbon atoms, 1 or 2 nitrogen atoms and one, two or three double bonds, the carbon atoms being unsubstituted or substituted by $C_1$–$C_4$-alkyl or halogen, and Z is an acid radical.

Suitable concentrates contain, for example,

5–40, in particular 6–12, % by weight of a zinc compound,

10–40, in particular 20–37, % by weight of a carboxylic acid/polycarboxylic acid, 5–40, in particular 15–30, % by weight of a polyamine, up to 25, in particular 2–7, % by weight of a complex-forming carboxylic acid, up to 40, in particular 4–6, % by weight of a diffusing fungicidal anion, up to 75, in particular 13–25, % by weight of a quaternary ammonium salt and up to 30, in particular 5–12, % by weight of a salt of N-cyclohexyldiazenium dioxide, the sum being 100% by weight in each case.

If necessary, minor amounts of other components, such as other amines, ammonia, wetting agents, water softeners (nitrilotriacetic acid, etc.) and, if necessary, water may be present, the amount of the water being kept as small as possible and essentially facilitating handling.

However, the present invention also embraces the impregnating solutions which can be prepared by diluting the concentrates with water in accordance with the required concentrations for use, regardless of the method of impregnation and the degree of danger to the wood, for example dilution to 2–6%, in particular 4%, based on the concentrate.

The concentrates, which may be in the form of pastes or viscous solutions (if necessary also in the form of a solid salt), are most advantageously prepared by initially taking the polyamine, with or without water, and first dissolving therein the carboxylic acids and, if required, the salts with fungicidal anions and/or salts of N-cyclohexyldiazenium dioxide. The zinc compounds then dissolve in this mixture with complex formation, the dissolution process being accelerated by heating to 90°–100° C. The alkalinity of the concentrates is adjusted so that, on the one hand, sufficient polyamine and, where relevant, complex-forming carboxylic acid are present to dissolve the zinc compound and, on the other hand, the pH of the dilute impregnating solutions is generally greater than 7.0, in particular from 8.0 to 9.0 (concentration-dependent), this being achieved by adding, for example, further polyamines, amine or alkali metal hydroxide. During impregnation, the zinc compound thoroughly penetrates the wood, the major part of the zinc (about 70–95%) being fixed in the wood.

Other fungicides, eg. furmecyclox or benodanil, tridemorph, $C_{12}$/$C_{14}$/$C_{16}$-alkyldimethylamine, or insecticides, eg. lindane, can also be added to the formulations, and, if necessary, can be incorporated with the addition of emulsifiers and solvents, for example oxyethylated nonylphenols.

Use for the protection of the wood may be effected, for example, depending on the degree of danger to the wood:

(a) by spraying the wood with the solution, (b) by dipping the wood into the solution, (c) by impregnating the wood with the aid of pressure differences, for example the pressure process or double vacuum impregnation, and (d) by painting the wood.

To test the stability, concentrates were prepared and were diluted with water to the concentration for use (for example for the pressure process). The stability and appearance of the solutions were determined. The solutions prevent destruction of the wood by fungi in the same manner as known solutions which contain copper instead of zinc.

KNOWN COMPARATIVE EXAMPLES

COMPARISON 1

30.00% of ethanolamine
36.00% of 2-ethylhexanoic acid
10.00% of zinc oxide
24.00% of water
The concentrate is cloudy even after prolonged heating at about 100° C.; at a use concentration of 4% (based on the concentrate), a cloudy solution with precipitate is obtained.

COMPARISON 2

30.00% of ethanolamine
35.00% of 2-ethylhexanoic acid
4.00% of lactic acid
10.00% of zinc oxide
21.00% of water
Clear concentrate.
Concentration for use 4%: cloudy solution, precipitation

EXAMPLES ACCORDING TO THE INVENTION

EXAMPLE 1

20.00% of diethylenetriamine
35.00% of 2-ethylhexanoic acid
10.00% of zinc oxide
35.00% of water
Clear concentrate.
Concentration for use 4%: clear solution, pH about 8.7.

EXAMPLE 2

20.00% of diethylenetriamine
34.00% of 2-ethylhexanoic acid
6.00% of lactic acid
10.00% of zinc oxide
15.00% of $C_{12}/C_{14}$-dimethylalkylbenzylammonium chloride
15.00% of water
Clear concentrate.
Concentration for use 4%: clear solution, pH about 8.5.

EXAMPLE 3

20.00% of diethylenetriamine
34.00% of 2-ethylhexanoic acid
6.00% of lactic acid
10.00% of zinc oxide
9.00% of the potassium salt of N-cyclohexyldiazenium dioxide
21.00% of water
Clear concentrate.
Concentration for use 4%: clear solution, pH about 8.6.

EXAMPLE 4

26.50% of aminoethylethanolamine
34.00% of 2-ethylhexanoic acid
6.00% of lactic acid
10.00% of zinc oxide
15.00% of $C_{12}/C_{14}$-dimethylalkylbenzylammonium chloride
8.50% of water
Clear concentrate.
Concentration for use 4%: clear solution, pH about 8.0.

EXAMPLE 5

28.50% of aminoethylethanolamine
35.00% of 2-ethylhexanoic acid
10.00% of zinc oxide
20.00% of $C_{12}/C_{14}$-dimethylalkylbenzylammonium chloride
6.50% of water
Clear concentrate.
Concentration for use 4%: clear solution, pH about 8.5.

EXAMPLE 6

25.00% of aminoethylethanolamine
31.00% of 2-ethylhexanoic acid
5.00% of lactic acid
9.00% of zinc oxide
9.00% of the potassium salt of N-cyclohexyldiazenium dioxide
21.00% of water
Clear concentrate.
Concentration for use 4%: clear solution, pH about 8.5.

EXAMPLE 7

25.00% of dipropylenetriamine
35.00% of 2-ethylhexanoic acid
6.00% of lactic acid
10.00% of zinc oxide
5.00% of boric acid
19.00% of water
Clear concentrate.
Concentration for use 4%: clear solution, pH about 8.9.

EXAMPLE 8

23.00% of dipropylenetriamine
33.00% of 2-ethylhexanoic acid
3.00% of lactic acid
9.00% of zinc oxide
15.00% of dimethylalkylbenzylammonium chloride
17.00% of water
Clear concentrate.
Concentration for use 4%: clear solution, pH about 8.8.

EXAMPLE 9

10.00% of aminoethylethanolamine
9.50% of dipropylenetriamine
25.00% of 2-ethylhexanoic acid
4.50% of lactic acid
7.50% of zinc oxide
5.00% of boric acid
7.50% of the potassium salt of N-cyclohexyldiazenium dioxide
31.00% of water
Clear concentrate.
Concentration for use 4%: clear solution, pH about 8.8.
We claim:

1. A wood preservative, consisting essentially of about 5 to 40% by weight of zinc metal or a zinc compound, about 10 to 40% by weight of a $C_5$–$C_{20}$ aliphatic mono- or di-carboxylic acid, and about 5 to 40% of a polyamine having 3 to 9 carbon atoms and 2 to 4 nitrogen atoms.

2. The wood preservative according to claim 1, wherein said $C_5$–$C_{20}$ monocarboxylic acid is selected from the group consisting of hexanoic acid, heptanoic acid, octanoic acid, nonanoic acid, decanoic acid, 2-ethylpentanoic acid, 2-ethylhexanoic acid, 2-ethylheptanoic acid, isooctanoic acid, isononanoic acid, and isodecanoic acid.

3. The wood preservative according to claim 1, wherein said $C_5$–$C_{20}$-dicarboxylic acid is decanedicarboxylic acid.

4. The wood preservative according to claim 1, wherein said polyamine is selected from the group consisting of 1,3-diaminopropane, dipropylenetriamine (3,3'-diaminodipropylamine), ethylenediamine, diethylenetriamine (2,2'-diaminodiethylamine) and aminoethylethanolamine.

5. The wood preservative according to claim 1, which further contains a complex-forming carboxylic acid selected from the group consisting of nitrilotriacetic acid and $C_3$–$C_6$-hydroxycarboxylic acids.

6. The wood preservative according to claim 1, which further contains a diffusible anion selected from the group consisting of a boride, fluoride and fluoborate anion.

7. The wood preservative according to claim 1, which further contains a zinc or potassium salt of N-cyclohexyldioxydiazenium oxide.

8. The wood preservative according to claim 1, wherein said $C_5$–$C_{20}$ monocarboxylic acid is 2-ethylhexanoic acid.

9. The wood preservative according to claim 5, wherein said $C_3$–$C_6$-hydroxycarboxylic acids are selected from the group consisting of lactic acid, tartaric acid and citric acid.

10. The wood preservative according to claim 1, which further contains a quaternary ammonium compound of the formula:

$$(R^1R^2R^3R^4N)^+Z^-$$

wherein $R^1$ is $C_8$–$C_{20}$ alkyl or benzyl which is unsubstituted or substituted by $C_1$–$C_{20}$ alkyl or halogen; $R^2$ is $C_1$–$C_6$ alkyl or $C_3$–$C_9$ alkoxyalkyl; $R^3$ is $C_1$–$C_6$ alkyl or $C_1$–$C_{14}$ alkoxy and $R^4$ is $C_1$–$C_{20}$ alkyl; or two of $R^1$, $R^2$, $R^3$ and $R^4$, together with the nitrogen atom, form a heterocyclic radical which contains 4 or 5 carbon atoms, 1 or 2 nitrogen atoms and one, two or three double bonds, the carbon atoms being unsubstituted or substituted by $C_1$–$C_4$ alkyl or halogen; and Z is an acid counteranion.

11. The wood preservative according to claim 1, wherein said zinc compound is selected from the group consisting of zinc sulfate, zinc hydroxide, zinc carbonate, zinc oxide, zinc acetate, zinc borate, zinc fluoride and zinc fluoroborate.

12. A process for preserving wood, which comprises treating wood with an impregnating solution which comprises a solution of the wood preservative of claim 1 in water.

13. An impregnating solution for preserving wood, which comprises a solution of the wood preservative of claim 5 in water.

14. The process according to claim 12, wherein said treating of wood comprises spraying wood with said solution, digging wood into said solution, impregnating wood with said solution and painting wood with said solution.

15. The process according to claim 12, wherein said solution has a concentration of said wood preservative of about 2 to 6% by weight.

16. The impregnating solution according to claim 13, which contains a concentration of said wood preservative of about 2 to 6% by weight.

* * * * *